United States Patent [19]

Bornstein et al.

[11] 3,949,064

[45] Apr. 6, 1976

[54] METHOD OF DETECTING ANTIGENS OR ANTIBODIES

[75] Inventors: Irene Bornstein, Skokie; Andreas A. Kapsalis, Northfield, both of Ill.

[73] Assignee: Baxter Laboratories, Inc., Deerfield, Ill.

[22] Filed: Oct. 26, 1973

[21] Appl. No.: 410,066

[52] U.S. Cl. ............... 424/1; 23/230 B; 250/303
[51] Int. Cl.² G01T 33/00; G01T 1/16; A61K 43/00
[58] Field of Search ............... 424/1; 23/230 B

[56] References Cited
UNITED STATES PATENTS

| 3,645,852 | 2/1972 | Axen et al. | 424/1 X |
| 3,646,346 | 2/1972 | Catt | 250/83 |
| 3,788,948 | 1/1974 | Kagedal et al. | 424/1 X |

FOREIGN PATENTS OR APPLICATIONS

| 2,164,705 | 3/1973 | France | 424/1 |

OTHER PUBLICATIONS

"Radioimmunoassays Employing Immunosorbents," in Acta Endocrinologia Supplementum, 63:142, 1969, pp. 207-221.

*Primary Examiner*—Benjamin R. Padgett
*Assistant Examiner*—Christine M. Nucker

[57] ABSTRACT

This disclosure concerns a solid phase method for detecting antigens or antibodies. An unknown sample is contacted with two sources of solid phase antigen. By treating each source in a particular manner it is possible to determine if the sample contains antigen or antibody.

11 Claims, No Drawings

METHOD OF DETECTING ANTIGENS OR ANTIBODIES

BACKGROUND OF THE INVENTION

This invention concerns a method for detecting substances (generally proteins) which are capable of acting as antigens or antibodies in blood plasma or serum samples. More particularly the invention is concerned with a method for detecting hepatitis associated antigens and antibodies. The invention uses radioimmunoassay (RIA) or radioimmunological techniques which are well known in the art. These techniques can be used for detecting the presence of a particular substance, e.g. antigen or antibody, by attaching a radioactive material or other marker to a specific antibody and then measuring the amount of such labeled antibody which binds or attaches to a solid phase antigen. In the case of radioactively labeled antibody, by measuring the amount of radioactive emissions from the unknown sample and comparing them with standard curves obtained using known amounts of antigen it is possible to determine if a plasma or serum sample contains a particular antigen or antibody.

Many RIA prior art techniques employed to detect the presence of antigens or antibodies, including hepatitis associated antigens and antibodies, first immobilize the antibody by attaching it to a solid phase or substrate. Examples of these techniques are described in the following references: U.S. Pat. No. 3,646,346 issued to Kevin J. Catt on Feb. 29, 1972; an article entitled "A Solid-Phase Radioimmunoassay for a Thermostable Adrenal-Specific Antigen" by I.O. Auer, Y. Yagi, R. Kasukawa and F. Milgrom (*Int. Arch. Allergy*, Vol. 42, pages 816–825, received for publication January 15, 1972); and an article entitled "Prevalence of Hepatitis B Virus Antigen as Revealed by Direct Radioimmune Assay with $^{125}$I-Antibody" by C. M. Ling and L. R. Overby, (*The Journal of Immunology*, Vol. 109, No. 4, October 1972, pages 834–841.

In contrast to the above art, in the invention described herein, the antigen is bound to the solid phase components. Prior art which describes similar techniques is described in articles entitled "Rapid Micro-Radioimmunoassay for the Measurement of Antiviral Antibody" by Joel D. Rosenthal, Kozaburo Hayashi and Abner Louis Notkins (*The Journal of Immunology*, Vol. 109, No. 1, pages 171–173, July, 1972); "Detection of Antibody to Hepatitis-Associated Antigen in Hemophilia Patients and in Voluntary Blood Donors" by M. R. Peterson, L. F. Barker and D. S. Schade (Vox Sanguinis, Vol. 24, pages 66–75, received for publication March, 1972) and an article entitled "'Sandwich' Solid Phase Radioimmunoassay for the Quantitative Determination of Human Immunoglobulins" by Sydney E. Salmon, Gail Mackey and H. Hugh Fudenberg (*The Journal of Immunology*, Vol. 103, No. 1, pages 129–137, July 1969; received for publication Nov. 25, 1968). Both of these techniques will detect only antigen or antibody, not both, and differ from the technique described here in other particulars.

SUMMARY OF THE INVENTION

This invention discloses a method for detecting the presence of proteins which are capable of acting as either antigens or antibodies. The method comprises contacting each unknown sample with two surfaces of solid phase antigen, that is, an antigen attached to a solid phase. The solid phase may be a test tube, or similar receptacle or it may be a solid particle carrier such as porous glass beads. For purposes of describing this invention the word "receptacle" will be used to mean any suitable, solid phase antigen carrier.

After the sample is added to the solid phase antigen, an amount of labeled antibody is added to one of the receptacles (hereafter called the "indicator" receptacle). At a given period of time later, the contents of the other receptacle (hereafter called the "discriminator" receptacle) are removed, the receptacle is washed, and an amount of labeled antibody equal to that added to the indicator receptacle is added. Both receptacles are then allowed to remain undisturbed for a predetermined period of time. The unbonded or unattached contents of each receptacle are then removed and the amount of radiation emitted by each receptacle is measured. By comparing the amounts of radiation emitted from each receptacle with negative controls or standard curves (made using known amounts of antigen or antibody) or by comparing the amounts of emitted radiation of the two receptacles with each other, it is then possible to determine whether the sample contains antigen or antibody.

DESCRIPTION OF THE INVENTION

This invention concerns a method of detecting substances capable of acting as antigens and antibodies. Prior to this invention it has been possible to detect only antigens or antibodies, not both, when using a single RIA technique.

The method of this invention comprises a number of steps. The first step is to coat with known antigen a pair of identical receptacles, such as test tubes or two equal amounts of solid particles, such as glass beads.

The receptacles may be made from a water-insoluble material such as polystyrene, polyethylene, polypropylene, nitrocellulose, acrylomide or copolymers of acrylonitrile with styrene. Small particles made of these materials can also be used to carry the antigen. These materials are selected because most proteins, and particularly hepatitis associated antigens will bond or attach to them.

To prepare the receptacles for use in the invention described herein, the desired antigen is attached to the surface of receptacles by simply contacting each receptacle with similar amounts of known antigen in solution. The pH of this antigen solution is maintained between 5 and 9 by adding suitable buffers. A portion of the antigen will thus become attached to the surface of the receptacles; this is referred to as the solid phase antigen. After allowing the known antigen to remain in contact with the receptacles for a predetermined period of time, the unattached contents of each receptacle are removed and each receptacle is washed. This leaves only known antigen attached to the receptacles. Alternatively, antigen may be attached to solid phase by appropriate chemical reactions, such as occur with cyanogen bromide activated cellulose.

At this point in the process the receptacles may be equilibrated by contacting them for a predetermined period of time with a bovine serum albumin or any other protein which is not of the same species as the antigen or antibody being tested. The equilibration step serves to fill in the receptors on the receptacle surfaces which have not been occupied by the known antigen thereby minimizing nonspecific protein adsorption during subsequent process steps. After equilibration, the excess equilibration solution is removed from the receptacle surfaces by washing and shaking dry. Coated receptacles are stable for several months when stored at 5°C.

To perform the assay which is the subject of this application, amounts of an unknown sample to be tested for the presence of antigen or antibody are added to two receptacles. In using the method of this invention for screening human blood for hepatitis associated antigen or antibody, the presence of antigen indicates the blood donor is a carrier of hepatitis while the presence of antibody indicates the donor has had hepatitis at some time.

After adding the samples, labeled antibody is added to the indicator receptacle only. A labeled antibody is a protein, capable of combining with a known antigen, and which has attached to it some radioactive material, for example, a radioactive isotope of iodine, such as $I^{125}$. Alternatively, an enzyme, such as alkaline phosphatase of horseradish peroxidase could be attached to the antibody to serve as a marker or label. A suitable technique for preparing labeled antibody is discussed in an article entitled "The Preparation of $I^{131}$ Labeled Human Growth Hormone of High Specific Radioactivity" by F. G. Greenwood, W. M. Hunter and J. S. Glover (*Biochem. J.*, Vol. 89, 1963, pages 114–123).

After incubating both tubes at room temperature for at least one hour, the contents of the discriminator tube are washed out, and labeled antibody is added. After a predetermined period of time, generally at least one hour, the contents of both tubes are discarded, both tubes are washed, and the radioactivity remaining in the tubes is determined by gamma counting.

After the radioactivity of each receptacle has been recorded the counts are compared with known negative controls. If the count in both receptacles is maximal as determined by utilization of known negative or normal samples it can be concluded that the sample being tested contains neither antigen nor antibody. If the count in the indicator receptacle is significantly lower than the maximal negative control count and the count in the discriminator receptacle is high or close to the negative control count the sample contains antigen. If the count in both receptacles is low in comparison to the negative control, the sample contains antibody.

The reasons for these conclusions are as follows. If the sample contains neither antigen nor antibody the count of both receptacles is high. The indicator receptacle count is high because the labeled antibody is free to combine with the solid phase antigen--therefore it does not bind to any antigen in the sample. The discriminator receptacle count is high because the labeled antibody freely binds to the solid phase antigen because no antibody in the sample has combined with the solid phase antigen prior to labeled antibody addition.

If the sample contains antigen the count of the indicator receptacle will be low because the antigen in the liquid sample competes with solid phase antigen for the limited quantity of labeled antibody added, thus reducing the amount of isotope ultimately attaching to the solid phase. Thus only small amounts of labeled antibody react with and become bonded to the solid phase antigen. On the other hand the count of the discriminator receptacle is high because the antigen in the sample does not attach to the solid phase antigen and is washed out prior to labeled antibody addition. Thus the labeled antibody added to the discriminator receptacle freely bonds to the solid phase antigen and causes the discriminator receptacle to have a radioactivity count equal to that of the negative control.

If the sample contains antibody both receptacles will have a low count. This is because in both receptacles the antibody in the sample will attach to the solid phase antigen and will limit substantially the amount of solid phase antigen available for combination with labeled antibody.

The method of this invention is particularly useful in detecting the presence of hepatitis associated antigens and antibodies. As opposed to all of the known antigen-antibody tests which detect either antigen or antibody, but not both, the method of this invention provides a method whereby either hepatitis associated antigen or antibody can be detected using a single test procedure.

Since the detection of hepatitis associated antigen and antibody are the preferred use of the inventive method, a procedure now will be specifically described where the protein being sought to be identified is hepatitis associated antigen or antibody. It should be understood however that the method of this invention can be used in any antigen-antibody system.

In one method of practicing the invention 10 × 75 millimeter polystyrene test tubes were used as the receptacles. The tubes were coated with 0.2 ml. of a purified hepatitis associated antigen solution. The solution had a pH of 7.4 and comprised approximately $10^{14}$ particles of hepatitis associated antigen per milliliter in 0.2 M ethylene diamine acetic acid buffer containing 0.001 M $MgCl_2$. The tubes were allowed to remain at room temperature overnight.

The next morning the antigen solution was removed from the tubes. They were then equilibrated with 1 ml. of 0.5% bovine albumin solution for four (4) hours. They were then rinsed with phosphate buffered saline (pH 7.2). At this stage in the process the tubes could be stored at about 5°C. for several months without loss of activity.

The hepatitis associated antibody was then labeled using $I^{125}$ in accordance with the techniques described in the article identified above by Greenwood et al. The antibody could alternatively be labeled with any easily detectable substance such as nitrophenyl groups which may be quantitated by electron spin resonance techniques, or with enzymes such as alkaline phosphatase of horseradish peroxidase.

To analyze plasma or serum samples the following procedure was then followed. 0.1 ml of an unknown sample was added to each of a pair of test tubes or receptacles prepared as described above. After one (1) hour at room temperature 0.1 ml. of the labeled antibody solution was added to one tube, hereafter called the "indicator" tube. At the same time the contents of the other tube, hereafter the "discriminator" tube, were removed.

The discriminator tube was washed several times with phosphate buffered saline (pH 7.2) and 0.1 ml of labeled antibody and 0.1 ml of phosphate buffered saline were added. The 0.1 ml of phosphate buffered saline affects the antigen-antibody reaction only insofar as it makes the volume of the discriminator receptacle equal to the volume of the indicator receptacle. This insures that the reaction in the discriminator tube will not vary in relation to the indicator tube because of volume differences.

After two hours the contents of both tubes were removed and the tubes washed. The tubes were then placed in a deep well gamma counter and their radioactivity measured. By comparing the CPM data for each tube it is possible to determine if antigen or antibody or neither antibody nor antigen is present in a sample.

Results using the above technique with a negative control, normal serum, i.e. serum known to contain no hepatitis associated antigen or antibody and samples from a National Institute of Health (NIH) panel known to contain hepatitis associated antigen or antibody are shown in Table I.

TABLE I

| Sample | CPM Indicator | CPM Discriminator | % of Normal Indicator | % of Normal Discriminator | Interpretation |
|---|---|---|---|---|---|
| Normal | 2519 | 3882 | 100 | 100 | Normal |
| Normal | 2345 | 3200 | | | |
| NIH Panel No. | | | | | |
| 234 | 747 | 3630 | 30.8 | 102.4 | Antigen |
| 243 | 1846 | 3677 | 76.0 | 103.7 | Antigen |
| 231 | 118 | 832 | 4.9 | 23.5 | Antibody |
| 248 | 15 | 2612 | 0.6 | 73.7 | Antibody |

NIH panel numbers 234 and 243 are serum samples known to contain hepatitis associated antigen. As discussed earlier an indicator tube CPM reading lower than the negative or normal control in combination with a discriminator tube CPM reading which is high or close to the negative control reading indicates that antigen is present in the tested sample. The CPM readings for NIH panel numbers 234 and 243 fit this pattern and therefore illustrate the ability of the method of this invention to detect antigen.

The ability of the inventive method to detect antibody is illustrated by the results obtained when NIH panel numbers 231 and 248 were tested. As previously discussed, low indicator and discriminator receptacle CPM readings in comparison to negative control CPM readings indicate the presence of antibody. The CPM readings obtained testing NIH panel numbers 231 and 248 confirmed that hepatitis associated antibody was contained in the samples.

The high CPM readings in both normal samples confirmed that neither antigen nor antibody was present in these samples.

Modifications and variations within the scope of the following claims are intended to be included.

We claim:

1. A method for detecting the presence of proteins in samples, wherein said proteins are capable of acting as antigens or antibodies, said method comprising:
   a. Coating at least a portion of the surface of a pair of water-insoluble receptacles with a known antigen;
   b. Adding sample to said pair of receptacles;
   c. Adding labelled antibody to one of the receptacles of said pair;
   d. Allowing said pair of receptacles to remain undisturbed for a predetermined period of time;
   e. Removing the contents of the other receptacle of said pair and then adding to said other receptacle an amount of labelled antibody equal to that added to said one receptacle in step (c);
   f. Allowing said pair of receptacles to remain undisturbed for a predetermined period of time;
   g. Removing the unbonded contents of each receptacle of said pair; and
   h. Measuring the amount of said labelled antibody in each receptacle, whereby the presence of said proteins can be detected.

2. The method of claim 1 in which in step (a) said antigen is hepatitis-associated antigen, and in step (c) said antibody is antibody to said hepatitis-associated antigen.

3. The method of claim 1 wherein said labelled antibody is labelled with nitrophenyl groups.

4. The method of claim 1 in which said labelled antibody is labelled with alkaline phosphatase of horseradish peroxidase.

5. A method for detecting the presence of proteins in samples, wherein said proteins are capable of acting as antigens or antibodies, said method comprising:
   a. coating at least a portion of the surface of a pair of water insoluble receptacles with a known antigen;
   b. adding sample to said pair of receptacles;
   c. adding radioactively labeled antibody to one of the receptacles of said pair;
   d. allowing said pair of receptacles to remain undisturbed for a predetermined period of time;
   e. removing the contents of the other receptacle of said pair and then adding to said other receptacle an amount of labeled antibody equal to that added to said one receptacle in step (c);
   f. allowing said pair of receptacles to remain undisturbed for a predetermined period of time;
   g. removing the unbonded contents of each receptacle of said pair;
   h. measuring the amount of emitted radiation of each receptacle;
   i. comparing the amounts of emitted radiation of the two receptacles with the amounts of emitted radiation of negative controls to determine whether the sample contains either antigen or antibody or neither antigen nor antibody.

6. The method of claim 5 in which in step (a) said antigen is hepatitis associated antigen and in step (c) said antibody is antibody to hepatitis associated antigen.

7. The method of claim 5 where in step (c) said labeled antibody is labeled with a radioactive isotope of iodine.

8. The method of claim 7 wherein said radioactive isotope of iodine is $I^{125}$.

9. The method of claim 5 wherein in steps (d) and (F) said predetermined period of time is sufficient to allow maximum binding of the materials in said receptacles to each other or to said receptacles.

10. The method of claim 5 wherein said water-insoluble material is a polymeric material selected from the group consisting of polystyrene, polyethylene, polypropylene, nitrocellulose, and copolymers of acrylonitrile with styrene.

11. The method of claim 5 wherein said water-insoluble material is glass beads.

* * * * *